(12) United States Patent
Tsuda et al.

(10) Patent No.: US 8,399,703 B2
(45) Date of Patent: Mar. 19, 2013

(54) COMPOUND, METHOD FOR PRODUCING THE SAME AND METHOD FOR PRODUCING FLUOROPOLYMER

(75) Inventors: Nobuhiko Tsuda, Settsu (JP); Akinari Sugiyama, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 371 days.

(21) Appl. No.: 12/668,168

(22) PCT Filed: Jul. 24, 2008

(86) PCT No.: PCT/JP2008/063252
§ 371 (c)(1),
(2), (4) Date: Jan. 7, 2010

(87) PCT Pub. No.: WO2009/014167
PCT Pub. Date: Jan. 29, 2009

(65) Prior Publication Data
US 2010/0197852 A1 Aug. 5, 2010

(30) Foreign Application Priority Data
Jul. 24, 2007 (JP) .................. 2007-192585

(51) Int. Cl.
*C07C 59/135* (2006.01)
*C07C 309/04* (2006.01)
(52) U.S. Cl. ........ 562/111; 562/113; 562/586; 526/209; 526/214; 526/225; 526/242; 524/805
(58) Field of Classification Search .................. 562/111, 562/113, 586; 524/544, 805; 526/242
See application file for complete search history.

(56) References Cited

U.S. PATENT DOCUMENTS

| 3,642,880 | A | * | 2/1972 | Sweeney ........................ 562/111 |
| 4,564,661 | A | | 1/1986 | Beresniewicz |
| 5,093,432 | A | * | 3/1992 | Bierschenk et al. ....... 525/331.6 |
| 6,429,258 | B1 | | 8/2002 | Morgan et al. |
| 7,041,728 | B2 | * | 5/2006 | Zipplies et al. ................ 524/544 |
| 2006/0276671 | A1 | * | 12/2006 | Harmer et al. ................. 562/120 |
| 2006/0281946 | A1 | | 12/2006 | Morita et al. |
| 2007/0015864 | A1 | | 1/2007 | Hintzer et al. |
| 2007/0015937 | A1 | * | 1/2007 | Hintzer et al. ................ 562/586 |
| 2007/0142541 | A1 | * | 6/2007 | Hintzer et al. ................ 524/544 |
| 2011/0034604 | A1 | * | 2/2011 | Hintzer et al. ................ 524/394 |

FOREIGN PATENT DOCUMENTS

| JP | 61-207413 A | | 9/1986 |
| JP | 10-212261 A | | 8/1998 |
| JP | 2003119204 A | * | 4/2003 |
| JP | 2005-36002 A | | 2/2005 |
| JP | 2005-036002 A1 | | 2/2005 |

OTHER PUBLICATIONS

Machine translation of JP 2003-119204 A, translated on Jan. 20, 2012.*

* cited by examiner

*Primary Examiner* — Nicole M Buie-Hatcher
(74) *Attorney, Agent, or Firm* — Sughrue Mion, PLLC

(57) ABSTRACT

The invention provides a compound which is useful in production of a fluoropolymer and easy to be removed from the produced fluoropolymer, a method of producing the compound, and a method of producing a fluoropolymer using the compound. The invention provides a compound which is represented by $Rf^1-CH_2O-CF_2-CHF-Rf^2-X$, wherein $Rf^1$ represents a fluoroalkyl group containing 1 to 5 carbon atoms, $Rf^2$ represents a fluoroalkylene group containing 1 to 3 carbon atoms, X represents $-COOM$ or $-SO_3M$, and M represents one of H, K, Na, and $NH_4$.

2 Claims, No Drawings

COMPOUND, METHOD FOR PRODUCING THE SAME AND METHOD FOR PRODUCING FLUOROPOLYMER

TECHNICAL FIELD

The invention relates to a novel compound, a method for producing the novel compound, and a method for producing a fluoropolymer.

BACKGROUND ART

A carboxylic acid containing a fluoroalkyl group such as ammonium perfluorooctanoate is thermally and chemically stable. The carboxylic acid can advantageously inhibit a side reaction such as a chain transfer when used in polymerization reactions, and therefore, it has been conventionally used as an emulsifier. However, there has been a problem that conditions for washing, heating and the like for removing the carboxylic acid from a resin obtained by a polymerization reaction are restricted within narrow limits.

A method of polymerizing tetrafluoroethylene (TFE) by using a tertiary perfluoroalkoxide as a surfactant in an aqueous medium, instead of using a fluorine-substituted carboxylic acid, is known as a method of producing a fluoropolymer (see Patent Document 1).

Recently disclosed as other methods of producing a fluoropolymer are a method of using a carboxylic acid having a fluoroalkyl group and an alkylene group containing 1 to 3 carbon atoms as a surfactant (see Patent Document 2), instead of a fluorine-substituted carboxylic acid, and a method of using a carboxylic acid having a fluoroalkyl group and an ether oxygen as a surfactant (see Patent Document 3), instead of a fluorine-substituted carboxylic acid.

As a surfactant which is easily removed from a resin obtained by polymerization, a material including a compound having a —(CF$_2$O)— structure is suggested (see Patent Document 4)

Patent Document 1: Japanese Kokai Publication S61-207413
Patent Document 2: Japanese Kokai Publication H10-212261
Patent Document 3: U.S. Pat. No. 6,429,258
Patent Document 4: U.S. patent application No. 2007/0015864

DISCLOSURE OF INVENTION

Problems Which the Invention is to Solve

It is an object of the invention to provide a compound which is useful in production of a fluoropolymer and easy to be removed from the produced fluoropolymer, a method of producing the compound, and a method of producing a fluoropolymer using the compound.

Means for Solving the Problems

The invention provides a compound which is represented by the formula:

$$Rf^1\text{—}CH_2O\text{—}CF_2\text{—}CHF\text{—}Rf^2\text{—}X$$

wherein $Rf^1$ represents a fluoroalkyl group containing 1 to 5 carbon atoms, $Rf^2$ represents a fluoroalkylene group containing 1 to 3 carbon atoms, X represents —COOM or —SO$_3$M, and M represents one of H, K, Na, and NH$_4$.

The invention provides a method of producing a fluorine-containing compound comprising the steps of:

(1) adding, to a compound (a1), a compound (a2) in an aqueous medium under an alkaline condition to obtain a compound (a3), the compound (a1) represented by CF$_2$=CF—Rf$^2$—X, wherein Rf$^2$ represents a fluoroalkylene group containing 1 to 3 carbon atoms, X represents —COOM or —SO$_3$M, and M represents one of H, K, Na, or NH$_4$, the compound (a2) represented by Rf$^1$—CH$_2$OH, wherein Rf$^1$ represents a fluoroalkyl group containing 1 to 5 carbon atoms and the compound (a3) represented by Rf$^1$—CH$_2$—O—CF$_2$—CHF—Rf$^2$—X, wherein Rf$^1$, Rf$^2$, and X are as defined above; and (2) fluorinating the compound (a3) to obtain the fluorine-containing compound, the fluorine-containing compound represented by Rf$^3$—O—CF$_2$—Rf$^4$—X, wherein Rf$^3$ represents a fluoroalkyl group containing 1 to 6 carbon atoms, Rf$^4$ represents a fluoroalkylene group containing 1 to 4 carbon atoms, and X is as defined above.

The invention provides a surfactant which includes the above compound of the invention.

The invention provides a surfactant for polymerization which includes the above compound of the invention.

The invention provides a method of producing a fluoropolymer, which includes polymerizing a fluoromonomer in an aqueous medium in the presence of the above compound of the invention.

The invention provides a fluoropolymer aqueous dispersion, wherein fluoropolymer particles having an average particle size of 50 to 500 nm are dispersed in an aqueous medium in the presence of the above compound of the invention.

The invention provides a method of producing the fluoropolymer aqueous dispersion, which includes the steps of:

(I) contacting an aqueous dispersion of a fluoropolymer with an anion exchange resin in the presence of a nonionic surfactant; and (II) concentrating the aqueous dispersion obtained in the step (I) so that the aqueous dispersion has a solid content concentration of 30 to 70% by mass with respect to 100% by mass of the aqueous dispersion.

The invention provides a fine powder of a fluoropolymer, which is obtained from the above fluoropolymer aqueous dispersion.

The invention provides a fine powder of a fluoropolymer, which is obtained by coagulating the fluoropolymer from the above fluoropolymer aqueous dispersion.

The invention provides a method of recovering a compound, which includes the steps of:

recovering the above compound of the invention from wastewater and/or gas generated in the step of producing the above fine powder; and purifying the recovered compound.

In the following, the invention is described in detail.

The compound of the invention is represented by the formula (1):

$$Rf^1\text{—}CH_2O\text{—}CF_2\text{—}CHF\text{—}Rf^2\text{—}X \qquad (1)$$

wherein $Rf^1$ represents a fluoroalkyl group containing 1 to 5 carbon atoms, $Rf^2$ represents a fluoroalkylene group containing 1 to 3 carbon atoms, X represents —COOM or —SO$_3$M, and M represents one of H, K, Na, and NH$_4$.

The compound of the invention has the following advantages.

The compound has $Rf^1$ and $Rf^2$ each containing the above defined number of carbon atoms, and has an acidic group such as —COOM. Accordingly, the compound is allowed to have excellent dispersibility and is suitably used as a surfactant, especially as a surfactant for polymerization.

Since the compound has the $Rf^1$—$CH_2O$— structure ($Rf^1$ is as defined above), when used in the production of a fluoropolymer, the compound is easily removed from the obtained polymer, which will be described later. In addition, fluorination of the compound provides a fluorine-containing compound which is excellent in dispersibility when used as an emulsifier.

In the formula (1), $Rf^1$ is preferably a fluoroalkyl group containing 1 to 3 carbon atoms.

Each of $Rf^1$ and $Rf^2$ may have the —$CH_2$— structure, provided that at least one fluorine atom is contained. When used as a surfactant for polymerization, each of $Rf^1$ and $Rf^2$ is preferably a perfluoro group so that the molecular weight of an obtained polymer is increased. In $Rf^1$, the carbon atom bound to —$CH_2O$— preferably contains a fluorine atom.

X is preferably —COOM.

M is preferably $NH_4$ in terms of good dispersibility.

The step (1) in the method of producing a fluorine-containing compound, which will be specifically described in the following, provides the compound of the invention as the compound (a3).

The method of producing a fluorine-containing compound of the invention includes the step (1) of adding, to the compound (a1), the compound (a2) in an aqueous medium under an alkaline condition to obtain the compound (a3). Here, the compound (a1) is represented by $CF_2$=$CF$—$Rf^2$—X (wherein $Rf^2$ and X are as defined above). The compound (a2) is represented by $Rf^1$—$CH_2OH$ (wherein $Rf^1$ is as defined above). The compound (a3) is represented by $Rf^1$—$CH_2$—O—$CF_2$—$CHF$—$Rf^2$—X (wherein $Rf^1$, $Rf^2$, and X are as defined above).

In accordance with the method of producing a fluorine-containing compound of the invention, the compound (a1) and the compound (a2) are reacted so that the compound (a3) as a novel compound is obtained.

In the production method, preferable examples of $Rf^1$, $Rf^2$ and X in the compounds (a1) and (a2) are the same as those described for the composition of the invention.

In the step (1), the reaction between the compounds (a1) and (a2) can be carried out, for example, at a temperature of 0° C. to 200° C. after mixing the compounds (a1) and (a2) in a ratio close to the stoichiometric mixture ratio.

The reaction is carried out under an alkaline condition. The alkaline condition refers to pH 9 or higher. This condition can be set by a conventionally known method, for example, by using an aqueous solution of an alkaline compound such as KOH.

In accordance with the method of producing a fluorine-containing compound of the invention, the compound (a3) is fluorinated in the step (2).

The fluorination can be carried out by a conventionally known method, such as a method in which the compound is contacted with fluorine gas and a method in which the compound is extruded under high shear force. The mode of the fluorination reaction can be appropriately selected in accordance with the number of carbon atoms contained in the compound (a3), a reaction scale of the compound (a3) and the like. The reaction is preferably carried out, for example, under the following conditions.

In the method in which the compound is contacted with fluorine gas, fluorine gas is preferably mixed with inert gas such as nitrogen and helium and used at a concentration of 10 to 50% by volume.

The contact with fluorine gas is preferably carried out at a temperature of 50° C. to 200° C. The contact with fluorine gas is preferably carried out under a pressure of 1 kPa to 0.1 MPa.

The method in which the compound is extruded under high shear force is not particularly restricted. Examples thereof include a method in which shear force is applied at extruding the compound by using a twin-screw extruder. When the extrusion is conducted, water or air is preferably supplied in order to efficiently fluorinate the compound.

The above described fluorination carried out in the step (2) provides the fluorine-containing compound represented by $Rf^3$—O—$CF_2$—$Rf^4$—X (wherein $Rf^3$ represents a fluoroalkyl group containing 1 to 6 carbon atoms, $Rf^4$ represents a fluoroalkylene group containing 1 to 4 carbon atoms, and X is as defined above).

In the fluorine-containing compound, $Rf^3$ is derived from $Rf^1$—$CH_2$— and $Rf^4$ is derived from —CHF—$Rf^2$. They may be fully fluorinated, or alternatively, partially fluorinated. For example, in the case of $Rf^1$ is $CF_3CF_2CF_2$—, $Rf^3$ may be $CF_3CF_2CF_2CF_2$— or $CF_3CF_2CF_2CHF$—, and further, $Rf^3$ may be $CF_3CF_2CF_2CH_2$—, provided that the other carbon atoms in the compound are fluorinated.

The fluorine-containing compound exhibits the following excellent properties.

The fluorine-containing compound is excellent in dispersibility, as the numbers of carbon atoms and the acidic group contained therein are as same as those in the compound of the invention.

When used in the production of a fluoropolymer, for example, the fluorine-containing compound is easily removed from the obtained polymer, as it has the $Rf^3$—O— structure ($Rf^3$ is as defined above).

In accordance with the method of producing a fluoropolymer of the invention, a fluoromonomer is polymerized in an aqueous medium in the presence of the above-described compound of the invention (hereinbelow, this compound is referred to as "compound (a)").

The total additive amount of the compound (a) is preferably 0.0001 to 2% by mass to the mass of the aqueous medium. A more preferable lower limit thereof is 0.001% by mass and a more preferable upper limit thereof is 0.5% by mass. At levels below 0.0001% by mass, dispersibility is likely to be insufficient. While the total additive amount exceeding 2% by mass will produce no further dispersing effect proportional to the additive amount, leading to lowering of the polymerization rate and stopping the reaction in some cases. The additive amount of the compound (a) is appropriately determined in accordance with the species of a fluoromonomer to be used, the molecular weight of the desired fluoropolymer and the like.

As the fluoromonomer, there may be mentioned, among others, fluoroolefins, preferably fluoroolefins containing 2 to 10 carbon atoms; fluorinated cyclic monomers; and fluorinated alkyl vinyl ethers represented by the formula $CY_2$=$CYOR^1$ or $CY_2$=$CYOR^2OR^3$ (in which Y is H or F, $R^1$ and $R^3$ each is an alkyl group containing 1 to 8 carbon atoms as resulting from substitution of a part or the whole of the hydrogen atoms by a fluorine atom or atoms, and $R^2$ is an alkylene group containing 1 to 8 carbon atoms as resulting from substitution of a part or the whole of the hydrogen atoms by a fluorine atom or atoms).

The fluoroolefin preferably contains 2 to 8 carbon atoms. As the fluoroolefin containing 2 to 8 carbon atoms, there may be mentioned, for example, tetrafluoroethylene [TFE], hexafluoropropylene [HFP], chlorotrifluoroethylene [CTFE], vinyl fluoride, vinylidene fluoride [VDF], trifluoroethylene, hexafluoroisobutylene and perfluorobutylethylene. As the fluorinated cyclic monomer, there may preferably be mentioned perfluoro-2,2-dimethyl-1,3-dioxole [PDD], perfluoro-2-methylene-4-methyl-1,3-dioxolane [PMD], etc.

Referring to the fluorinated alkyl vinyl ether, each of $R^1$ and $R^3$ preferably contains 1 to 4 carbon atoms and, more preferably, is the one resulting from substitution of all the hydrogen atoms by fluorine atoms, while $R^2$ preferably contains 2 to 4 carbon atoms and, more preferably, is the one resulting from substitution of all the hydrogen atoms by fluorine atoms.

As the fluorine-free monomer, there may be mentioned a hydrocarbon monomer reactive with the fluoromonomer. As the hydrocarbon monomer, there may be mentioned, among others, alkenes such as ethylene, propylene, butylene and isobutylene; alkyl vinyl ethers such as ethyl vinyl ether, propyl vinyl ether, butyl vinyl ether, isobutyl vinyl ether and cyclohexyl vinyl ether; vinyl esters such as vinyl acetate, vinyl propionate, vinyl n-butyrate, vinyl isobutyrate, vinyl valerate, vinyl pivalate, vinyl caproate, vinyl caprylate, vinyl caprate, vinyl versatate, vinyl laurate, vinyl myristate, vinyl palmitate, vinyl stearate, vinyl benzoate, vinyl p-tert-butylbenzoate, vinyl cyclohexanecarboxylate, vinyl monochloroacetate, vinyl adipate, vinyl acrylate, vinyl methacrylate, vinyl crotonate, vinyl sorbate, vinyl cinnamate, vinyl undecylenate, vinyl hydroxyacetate, vinyl hydroxypropionate, vinyl hydroxybutyrate, vinyl hydroxyvalerate, vinyl hydroxyisobutyrate and vinyl hydroxycyclohexanecarboxylate; alkyl allyl ethers such as ethyl allyl ether, propyl allyl ether, butyl allyl ether, isobutyl allyl ether and cyclohexyl allyl ether; and alkyl allyl esters such as allyl acetate, allyl propionate, allyl butyrate, allyl isobutyrate and allyl cyclohexanecarboxylate.

The fluorine-free monomer may also include a functional group-containing hydrocarbon monomer. As the functional group-containing hydrocarbon monomer, there may be mentioned, for example, hydroxyalkyl vinyl ethers such as hydroxyethyl vinyl ether, hydroxypropyl vinyl ether, hydroxybutyl vinyl ether, hydroxyisobutyl vinyl ether and hydroxycyclohexyl vinyl ether; carboxyl group-containing, fluorine-free monomers such as itaconic acid, succinic acid, succinic anhydride, fumaric acid, fumaric anhydride, crotonic acid, maleic acid, maleic anhydride and perfluorobutenoic acid; glycidyl group-containing, fluorine-free monomers such as glycidyl vinyl ether and glycidyl allyl ether; amino group-containing, fluorine-free monomers such as aminoalkyl vinyl ethers and aminoalkyl allyl ethers; and amide group-containing, fluorine-free monomers such as (meth)acrylamide and methylolacrylamide.

The polymerization in the invention is conducted as follows. A polymerization reactor is charged with an aqueous medium, the compound (a), the fluoromonomer, and other additives (if needed). The mixture in the polymerization reactor is stirred and the reactor is held at a predetermined polymerization temperature. Then, a polymerization initiator is added so as to start the polymerization reaction. After the start of the polymerization reaction, the fluoromonomer, the polymerization initiator, a chain transfer agent, and the compound (a) may be additionally added in accordance with the purpose of the reaction.

The aqueous medium is a reaction medium for polymerization and refers to a liquid which contains water. The aqueous medium is not particularly restricted, as long as it contains water. Examples thereof may include a medium containing: water; and a fluorine-free organic solvent, such as alcohols, ethers, and ketones, and/or a fluorine-containing organic solvent having a boiling point of 40° C. or lower.

The polymerization initiator is not particularly restricted, as long as it generates a radical in the above range of the polymerization temperature. A known oil-soluble and/or water-soluble polymerization initiator may be used. Further, a redox system resulting from combined use of the polymerization initiator and a reducing agent may be used to initiate the polymerization. The concentration of the polymerization initiator is appropriately determined in accordance with the species of the monomer, the molecular weight of the desired polymer, and the rate of reaction.

In accordance with the method of producing a fluoropolymer of the invention, it is possible to produce a fluoropolymer efficiently by using at least one of the compounds (a) mentioned above as a surfactant. In carrying out the method of producing a fluoropolymer of the invention, a certain compound having surfactant activity other than the compound (a) may also be used simultaneously if it is volatile or the remains thereof in fluoropolymer moldings or the like are allowable.

The other compound having surfactant activity is not particularly restricted but may be any of anionic, cationic, nonionic or betaine-type surfactants, for instance, and these surfactants may be hydrocarbon types.

In the above polymerization, the polymerization temperature is generally 5° C. to 120° C. and the polymerization pressure is generally 0.05 to 10 MPaG. The polymerization temperature and polymerization pressure are to be appropriately selected according to the fluoromonomer species employed, the molecular weight of the desired polymer and the rate of reaction.

The above polymerization provides a fluoropolymer aqueous dispersion containing 5 to 45% by mass of fluoropolymer particles having an average primary particle size of 50 to 500 nm.

In the present description, the average primary particle size is obtained indirectly from the transmittance, per unit length of the fluoropolymer aqueous dispersion, of the incident light of 550 nm through the fluoropolymer aqueous dispersion adjusted to the solid content concentration of the fluoropolymer of 0.22% by mass, based on a working curve constructed by plotting such transmittance data against the average primary particle size obtained from a transmission electron microscopy photomicrograph.

The concentration of the fluoropolymer particles is obtained as follows. An amount of 1 g of the aqueous dispersion is dried in an air dryer at 150° C. for 60 minutes and the proportion of the mass of nonvolatile content with respect to the mass (1 g) of the aqueous dispersion was obtained and expressed as a percentage.

The fluoropolymer is the one obtained by polymerizing the fluoromonomer and, in accordance with the intended purpose, the fluorine-free monomer may be copolymerized with the fluoropolymer.

As a fluoropolymer suitably producible by the production method according to the invention, there may be mentioned TFE polymers in which the monomer showing the highest mole fraction (hereinafter, "most abundant monomer") among the monomers constituting the polymer is TFE, VDF polymers in which the most abundant monomer is VDF, CTFE polymers in which the most abundant monomer is CTFE, and so forth.

The TFE polymer may suitably be a polytetrafluoroethylene (PTFE) polymer such as TFE homopolymers, a copolymer derived from (1) TFE; (2) one or more fluoromonomers other than TFE containing 2 to 8 carbon atoms, in particular HFP or CTFE, and/or (3) some other monomers. As the other monomers (3), there may be mentioned, for example, fluoro (alkyl vinyl ether) species containing 1 to 5 carbon atoms, in particular 1 to 3 carbon atoms; fluorodioxoles; perfluoroalkylethylenes; and ω-hydroperfluoroolefins.

The TFE polymer may further be a copolymer of TFE and one or more fluorine-free monomers. As the fluorine-free monomer, there may be mentioned, for example, alkenes such as ethylene and propylene; vinyl esters; and vinyl ethers. The TFE polymer may further be a copolymer derived from TFE, one or more fluoromonomers containing 2 to 8 carbon atoms, and one or more fluorine-free monomers.

The VDF polymer may suitably be a VDF homopolymer [PVDF] or a copolymer derived from (1) VDF, (2) one or more fluoroolefins other than VDF containing 2 to 8 carbon atoms, in particular TFE, HFP and/or CTFE, and (3) a perfluoro(alkyl vinyl ether) having an alkyl group containing 1 to 5 carbon atoms, in particular 1 to 3 carbon atoms, among others.

The CTFE polymer may suitably be a CTFE homopolymer or a copolymer derived from (1) CTFE, (2) one or more fluoroolefins other than CTFE containing 2 to 8 carbon atoms, in particular TFE and/or HFP, and (3) a perfluoro(alkyl vinyl ether) containing an alkyl group containing 1 to 5 carbon atoms, in particular 1 to 3 carbon atoms.

The CTFE polymer may also be a copolymer derived from CTFE and one or more fluorine-free monomers. Included among the fluorine-free monomers are alkenes such as ethylene and propylene; vinyl esters; and vinyl ethers.

In the production method according to the invention, after the above-described polymerization, an obtainable fluoropolymer may be subjected to concentration or dispersion stabilization so that an aqueous dispersion thereof is prepared, or alternatively, the fluoropolymer may be recovered by coagulation or flocculation and dried so that a powder or other solid forms are prepared.

As a method of concentration, a known method such as phase separation, electrical isolation and ultrafiltration may be mentioned. The concentration can adjust the fluoropolymer concentration to 30% to 70% by mass. The stability of the dispersion may be impaired upon concentration but, in such a case, a dispersion stabilizer may be further added. The above-mentioned compound (a) or any of various surfactants may be added as the dispersion stabilizer. The various dispersion stabilizers include, but are not limited to, nonionic surfactants such as polyoxyalkyl ethers, in particular polyoxyethylene alkylphenyl ethers (e.g. Triton X-100 (trademark), product of Rohm & Haas), and polyoxyethylene isotridecyl ether (NOIGEN TDS80C (trademark), product of DAI-ICHI KOGYO SEIYAKU CO., LTD.; LEOCOL TD90D (trademark), product of LION Corporation; GENAPOL X080 (trademark), product of Clariant (Japan) K.K.).

The total amount of the dispersion stabilizers corresponds to a concentration of 0.5 to 20% by mass relative to the solids content of the dispersion. At levels below 0.5% by mass, the dispersion stability may be poor in certain cases, while the total amount exceeding 20% by mass will produce no further dispersing effect proportional to their abundance, hence are impractical. A more preferred lower limit to the total amount of the dispersion stabilizers is 2% by mass, and a more preferred upper limit is 12% by mass.

The aqueous dispersion obtained by carrying out the polymerization mentioned above, without concentration, can be subjected to dispersion stabilization treatment according to the intended use thereof so that a fluoropolymer aqueous dispersion with a long pot life may be prepared. As the dispersion stabilizer to be used, there may be mentioned the same ones as those mentioned hereinabove.

A fluoropolymer producible by the production method according to the invention can be a glass, plastic, or elastomeric fluoropolymer. These are amorphous or partially crystalline, and can be subjected to compression sintering processing, melt processing, or non-melt processing.

The production method according to the invention can suitably be applied to the production of, for example, polytetrafluoroethylene polymers [TFE polymers] as non-melt processible resins (I), ethylene/TFE copolymers [ETFEs], TFE/HFP copolymers [FEPs] and TFE/perfluoro(alkyl vinyl ether) copolymers [PFAs, MFAs, etc.] as melt processible resins (II) and, as elastomeric copolymers (III), TFE/propylene copolymers, TFE/propylene/third monomer copolymers (the third monomer being VDF, HFP, CTFE, a perfluoro(alkyl vinyl ether) or the like), TFE/perfluoro(alkyl vinyl ether) copolymers; HFP/ethylene copolymers, HFP/ethylene/TFE copolymers; PVDF; VDF/HFP copolymers, HFP/ethylene copolymers, VDF/TFE/HFP copolymers and like thermoplastic elastomers; and fluorine-containing segmented polymers described in Japanese Patent Publication (Kokoku) S61-49327.

The perfluoro(alkyl vinyl ether) referred to above is represented by the formula:

$_{k3}OCF=CF_2$ wherein $Rf^5$ represents a perfluoroalkyl group containing 1 to 6 carbon atoms; k1, k2 and k3 are the same or different and each represents an integer of 0 to 5; $Q^1$, $Q^2$ and $R^4$ are the same or different and each represents F or $CF_3$.

The above-mentioned non-melt processible resins (I), melt processible resins (II) and elastomeric polymers (III) suitably producible by the method of producing a fluoropolymer according to the invention are preferably produced in the following manner.

(I) Non-Melt Processible Resin

In carrying out the production method of the TFE polymer of the invention, the polymerization for producing the TFE polymer is generally carried out at a polymerization temperature of 10 to 100° C. and a polymerization pressure of 0.05 to 5 MPa.

In the above polymerization, a pressure-resistant reaction vessel equipped with a stirrer is charged with pure water and the compound (a) of the invention and, after deoxygenation, further charged with TFE, the temperature is raised to a predetermined level, and a polymerization initiator is added to initiate the reaction. Since otherwise the pressure lowers with the progress of the reaction, an additional quantity of TFE is fed to the reaction vessel continuously or intermittently so as to maintain the initial pressure. After completion of feeding of a predetermined amount of TFE, the feeding is stopped, the TFE remaining in the reaction vessel is purged, and the temperature is returned to room temperature. The reaction is thus finished.

In the present specification, the term "polytetrafluoroethylene polymer [TFE polymer]" conceptually includes not only TFE homopolymers but also those copolymers of TFE and a modifying monomer(s) which are non-melt-processible (hereinafter referred to as "modified PTFEs").

In the production of the TFE polymer, various modifying monomers may be used.

As the modifying monomers, there may be mentioned, among others, perhaloolefins such as HFP and CTFE; fluoro(alkyl vinyl ether) species having an alkyl group containing 1 to 5, in particular 1 to 3, carbon atoms; fluorinated cyclic monomers such as fluorodioxole; perhaloalkylethylenes; and ω-hydroperhaloolefins. The modifying monomer feeding may be carried out initially all at once, or continuously, or intermittently in portions, according to the intended purpose and the feeding of TFE.

The modifying monomer content in the modified PTFEs is generally within the range of 0.001 to 2 mole percent.

In producing the TFE polymer, persulfate salts (e.g. ammonium persulfate) or organic peroxides such as disuccinoyl peroxide and diglutaroyl peroxide may be used as the polymerization initiator, either singly or in the form of a mixture of these. These may also be used in combination with a reducing agent such as sodium sulfite to give redox systems. Further, during polymerization, the radical concentration in the system can be adjusted by adding a radical scavenger such as hydroquinone or catechol or a peroxide-decomposing agent such as ammonium sulfite.

In producing the TFE polymer, use can be made of any of the known chain transfer agents, for example saturated hydrocarbons such as methane, ethane, propane and butane, halogenated hydrocarbons such as chloromethane, dichloromethane and difluoromethane, alcohols such as methanol and ethanol, and hydrogen. Those which are gaseous at ordinary temperature and ordinary pressure are preferred. The chain transfer agent is generally used in an amount of 1 to 1000 ppm, preferably 1 to 500 ppm, relative to the total feed of TFE.

In producing the TFE polymer, use can further be made, as a dispersion stabilizer for the reaction system, of 2 to 10 parts by mass, per 100 parts by mass of the aqueous medium, of a saturated hydrocarbon which contains not less than 12 carbon atoms, is substantially inert to the reaction and occurs as a liquid under the reaction conditions mentioned above. Furthermore, ammonium carbonate, ammonium phosphate or the like may be added as a buffering agent for adjusting the pH during reaction.

At the time of completion of the polymerization of the TFE polymers, aqueous dispersions having a solid content concentration of 10 to 50% by mass and including TFE polymer particles having an average particle size of 0.05 to 0.5 μm or, in particular when the compound (a) is used, including very small TFE polymer particles not larger than 0.3 μm in size can be obtained. The TFE polymers at the time of completion of the polymerization have a number average molecular weight of 1,000 to 10,000,000.

The aqueous TFE polymer dispersion obtained by the above-mentioned polymerization, when supplemented with a nonionic surfactant, is stabilized and, after further concentration, is preferably used in various fields of application in the form of a composition supplemented with an organic or inorganic filler(s) according to the intended purpose. The above composition, when applied to metal or ceramic substrates, can give coated surfaces having nonstickiness and a low coefficient of friction and excellent in gloss, wear resistance, weather resistance and heat resistance. Thus, it is suited for use in coating rolls and cooking utensils and impregnating processing of glass cloths.

The above-mentioned TFE polymer aqueous dispersion or the fine powder mentioned below is also preferably used as a processing aid. In the case of use thereof as a processing aid, the aqueous dispersion or fine powder mentioned above is admixed with a host polymer, for instance, whereby the host polymer is improved in melt strength on the occasion of melt processing thereof and/or the resulting polymer composition obtained may show improvements in mechanical strength, electrical characteristics, flame retardancy, anti-dripping performance and sliding property.

The TFE polymer aqueous dispersion or the fine powder mentioned below is also preferably used as the processing aid in the form of a composite material together with a resin other than the TFE polymer. The TFE polymer aqueous dispersion or TFE polymer fine powder is suited for use as a raw material for the production of those PTFEs which are described in Japanese Kokai Publications H11-49912 and 2003-24693, U.S. Pat. No. 5,804,654 and Japanese Kokai Publications H11-29679 and 2003-2980. The processing aid comprising the above-mentioned aqueous dispersion or fine powder is not inferior at all to the processing aids described in the respective publications cited above.

The TFE polymer aqueous dispersion mentioned above is also preferably processed by admixing the same with an aqueous dispersion of a melt-processible fluoropolymer, followed by coagulation, to give a co-coagulated powder. This co-coagulated powder is suited for use as a processing aid.

As the melt-processible fluoropolymer, there may be mentioned, for example, FEP, PFA, ETFE and EFEP resins. Among them, FEPs are preferred.

The fluorine-free resin to which the above co-coagulated powder is to be added may be in the form of a powder, pellets or an emulsion. The addition is preferably carried out under shearing force application by such a known method as extrusion kneading or roll kneading from the viewpoint of sufficient mixing up of the respective resins.

The TFE polymer aqueous dispersion mentioned above is also preferably used as a dust-control treatment agent. This dust-control treatment agent can be used in the method of inhibiting a dust-emitting substance from emitting dust by admixing the aqueous dispersion with the dust-emitting substance and subjecting the resulting mixture to compression-shearing action at a temperature of 20 to 200° C. to thereby fibrillate the TFE polymer, for example in carrying out the method described in Japanese Patent No. 2827152 or Japanese Patent No. 2538783.

The dust-control treatment agent mentioned above is suitably used in dust control treatment in the fields of building and construction, soil stabilizers, solidifying agents, fertilizers, landfill of incineration ash and hazardous substances, explosion protection, cosmetics and so forth.

The TFE polymer aqueous dispersion mentioned above is also suitably used as a raw material for obtaining a TFE polymer fiber by dispersion spinning method. The dispersion spinning method is a method of obtaining TFE polymer fibers by admixing the TFE polymer aqueous dispersion with an aqueous dispersion of a matrix polymer, subjecting the resulting mixture to extrusion processing to form an intermediate fibrous structure and baking the intermediate fibrous structure to thereby cause decomposition of the matrix polymer and sintering of TFE polymer particles.

It is also possible to produce a high-molecular-weight PTFE using the compound (a) mentioned above. The high-molecular-weight PTFE powder obtained by emulsion polymerization is also useful as a raw material for producing a porous PTFE article (membrane). For example, a porous PTFE article (membrane) can be obtained by subjecting the high-molecular-weight PTFE powder to paste extrusion, followed by rolling, and stretching the rolled intermediate product in a non-baked or half-baked condition in at least one direction (preferably stretching it by rolling in the direction of rolling, followed by stretching on a tenter in the width direction). Stretching makes the PTFE easy to fibrillate and give a porous PTFE article (membrane) consisting of knots and fibers.

This porous PTFE article (membrane) is useful as a filter for various purposes and can be suitably used as a filter for liquid chemicals and as an air filter medium, in particular.

It is also possible to polymerize a low-molecular-weight PTFE using the compound (a) mentioned above.

The low-molecular-weight PTFE species having a molecular weight of 600,000 or below (also called PTFE micropowders) are excellent in chemical stability and very low in surface energy and, in addition, hardly fibrillate and, therefore, are suited for use as an additive for achieving improvements in lubricant properties and/or in coat surface texture in manufacturing plastic products, inks, cosmetics, coatings, greases and so forth (cf. e.g. Japanese Kokai Publication H10-147617).

The low-molecular-weight PTFE may also be obtained by dispersing the polymerization initiator and the above-mentioned compound (a) as an emulsifier in the aqueous medium in the further presence of the chain transfer agent, followed by polymerizing TFE or TFE and a monomer(s) copolymerizable therewith in the resulting medium.

In the case of using the low-molecular weight PTFE obtained by emulsion polymerization in the forms of powder, the aqueous dispersion may be coagulated to obtain a powder particle (micro powder).

An unbaked tape (unsintered tape) can also be obtained from the fine PTFE powder obtained by using the compound (a) mentioned above.

(II) Melt-Processible Resin (1) In the production method of the invention, the polymerization for producing FEP is generally preferably carried out at a polymerization temperature of 60 to 100° C. and a polymerization pressure of 0.7 to 4.5 MPa.

The monomer composition (on the % by mass basis) of the FEP is preferably TFE:HFP=(60 to 95):(5 to 40), more preferably (85 to 90):(10 to 15). The FEP may be ones modified with a perfluoro(alkyl vinyl ether) as a third component used in a proportion within the range of 0.5 to 2% by mass of the total amount of the monomers.

In the above-mentioned FEP production by polymerization, such a chain transfer agent as cyclohexane, methanol, ethanol, carbon tetrachloride, chloroform, methylene chloride or methyl chloride is preferably used, and such a pH buffering agent as ammonium carbonate or disodium hydrogenphosphate is preferably used.

(2) In the production method of the invention, the polymerization for producing a TFE/perfluoro(alkyl vinyl ether) copolymer, such as PFA and MFA copolymers, is preferably carried out generally at a polymerization temperature of 60 to 100° C. and a polymerization pressure of 0.7 to 2.5 MPaG.

Preferred as the monomer composition (in mole percent) for the TFE/PAVE copolymer is TFE:PAVE=(95 to 99.7):(0.3 to 5), more preferably (98 to 99.5):(0.5 to 2). Preferably used as the PAVEs are those represented by the formula: $CF_2=CFORf$ (in which Rf is a perfluoroalkyl group containing 1 to 6 carbon atoms).

In the above-mentioned TFE/PAVE copolymer production by polymerization, such a chain transfer agent as cyclohexane, methanol, ethanol, carbon tetrachloride, chloroform; methylene chloride, methyl chloride, methane or ethane is preferably used, and such a pH buffering agent as ammonium carbonate or disodium hydrogenphosphate is preferably used.

(3) In the production method of the invention, the polymerization for producing the ETFE copolymer is generally preferably carried out at a polymerization temperature of 20 to 100° C. and a polymerization pressure of 0.5 to 0.8 MPaG.

Preferred as the monomer composition (in mole percent) of the ETFE is TFE:ethylene=(50 to 99):(50 to 1). The ETFE may be those modified with a third monomer in a proportion within the range of 0 to 20% by mass of the total amount of the monomers. The ratio is preferably TFE:ethylene:third monomer=(63 to 94):(27 to 2):(4 to 10). Preferred as the third monomer is perfluoro(butylethlene), 2,3,3,4,4,5,5-heptafluoro-1-pentene ($CH_2=CFCF_2CF_2CF_2H$) and 2-trifluoromethyl-3,3,3-trifluoropropene (($CF_3)_2C=CH_2$).

In the ETFE production by polymerization, such a chain transfer agent as cyclohexane, methanol, ethanol, carbon tetrachloride, chloroform, methylene chloride or methyl chloride is preferably used.

(4) By utilizing the fluoropolymer production method of the invention, it is also possible to produce an electrolyte polymer precursor. The electrolyte polymer precursor production by polymerization according to the fluoropolymer production method of the invention is preferably carried out at a polymerization temperature of 20 to 100° C. and a polymerization pressure of 0.3 to 2.0 MPaG. The electrolyte polymer precursor is a precursor which comprises such a vinyl ether monomer as specified below and is capable of being converted to an ion-exchange polymer via a hydrolysis treatment step.

As the vinyl ether monomer to be used in the electrolyte polymer precursor, there may be mentioned fluoromonomers represented by the formula:

wherein $Y^1$ represents fluorine atom, chlorine atom or a perfluoroalkyl group, n represents an integer of 0 to 3 and the each of n of $Y^1$ may be the same or different, $Y^2$ represents fluorine or chlorine atom, m represents an integer of 1 to 5 and the each of m of $Y^2$ may be the same or different, and A represents $—SO_2X^1$ and/or $—COZ^1$ in which $X^1$ represents a halogen atom and $Z^1$ represents an alkoxyl group containing 1 to 4 carbon atoms. The electrolyte polymer precursor preferably has a monomer composition (mole percent) of TFE: vinyl ether=(50 to 93):(50 to 7).

The above-mentioned electrolyte polymer precursor may be the one modified with a third monomer used in an amount within the range of 0 to 20% by mass of the total amount of the monomers.

As the third monomer, there may be mentioned CTFE, vinylidene fluoride, perfluoro(alkyl vinyl ether) species, and divinylbenzene and other polyfunctional monomers.

The thus-obtained electrolyte polymer precursor is molded into a membrane shape, for instance, and then subjected to hydrolysis with an alkali solution followed by mineral acid treatment for use as a polymer electrolyte membrane in a fuel cell, among others.

(III) Elastomeric Polymer

In carrying out the polymerization for producing a elastomeric polymer according to the method of the invention, a pressure-resistant reaction vessel equipped with a stirrer is charged with pure water and the compound (a) of the invention and, after deoxygenation, further charged with the monomers, the temperature is raised to a predetermined level, and a polymerization initiator is added to initiate the reaction. Since otherwise the pressure lowers with the progress of the reaction, additional quantities of the monomers are fed to the reaction vessel continuously or intermittently so as to maintain the initial pressure. After completion of feeding of predetermined amounts of the monomers, the feeding is stopped, the monomers remaining in the reaction vessel are purged away, and the temperature is returned to room temperature. The reaction is thus finished. In the case of emulsion polymerization, a polymer latex formed is preferably taken out of the reaction vessel continuously.

In particular when a thermoplastic elastomer is to be produced, it is also possible to employ the method of accelerating the eventual rate of polymerization as compared with a conventional polymerizations by synthesizing fine fluoropolymer particles once in the presence of the above-mentioned compound (a) at high concentration and, after dilution, further carrying out the polymerization, as disclosed in International Publication WO 00/01741.

In producing the elastomeric polymer, the reaction conditions are to be properly selected from the viewpoint of desired physical properties of the polymer and of a polymerization rate control. For example, the polymerization is carried out generally at a polymerization temperature of −20 to 200° C., preferably 5 to 150° C., and generally at a polymerization pressure of 0.5 to 10 MPaG, preferably 1 to 7 MPaG. Preferably, the pH of the polymerization medium is maintained generally at 2.5 to 9 with a pH adjusting agent, which is to be described later herein, in a conventional manner, for instance.

As the monomer to be used in producing the elastomeric polymers, there may be mentioned vinylidene fluoride as well as fluorine-containing, ethylenically unsaturated monomers containing at least the same number of fluorine atoms as the number of carbon atoms and capable of copolymerizing with vinylidene fluoride.

As the fluorine-containing ethylenically unsaturated monomers, there may be mentioned, among others, trifluoropropene, pentafluoropropene, hexafluorobutene and octafluorobutene. Among them, hexafluoropropene is particularly suited for use in view of the characteristics of an elastomer obtainable when it blocks the polymer crystal growth. As the fluorine-containing, ethylenically unsaturated monomers, there may further be mentioned trifluoroethylene, TFE, CTFE, etc., and fluorine-containing monomers having one or more chlorine and/or bromine substituents may also be used. PAVE, for example perfluoro(methyl vinyl ether), can also be used. TFE and HFP are preferred for the production of the elastomeric polymer.

The elastomeric polymer preferably has a monomer composition (in % by mass) of vinylidene fluoride:HFP:TFE= (20-70):(30-48):(0-32). The elastomeric polymer the composition of which is within this range shows good elastomer characteristics, chemical resistance and thermal stability.

In the polymerization of the elastomeric polymer, any of inorganic radical polymerization initiators known in the art can be used as the polymerization initiator. Those water-soluble inorganic peroxides known in the art, for example sodium, potassium and ammonium persulfate, perphosphate, perborate, percarbonate and permanganate, are particularly useful as the inorganic radical polymerization initiator. The radical polymerization initiator can be further activated by a reducing agent such as sodium, potassium or ammonium sulfite, bisulfite, metabisulfite, hyposulfite, thiosulfate, phosphite or hypophosphite, or by a readily oxidizable metal compound such as a ferrous salt, cuprous salt or silver salt. Ammonium persulfate is a suitable inorganic radical polymerization initiator, and the combined use of ammonium persulfate and sodium bisulfite in a redox system is more preferred.

The level of addition of the polymerization initiator is to be properly selected according to a desired molecular weight of the polymer and the rate of the polymerization reaction; generally, it is set at 0.0001 to 10% by mass, preferably 0.01 to 5% by mass of the total amount of the monomers.

In the polymerization of the above elastomeric polymers, any of a chain transfer agent known in the art can be used. In the case of PVDF polymerization, hydrocarbons, esters, ethers, alcohols, ketones, chlorine compounds, carbonates or the like can be used and, in the case of a thermoplastic elastomer, hydrocarbons, esters, ethers, alcohols, chlorine compounds, iodine compounds or the like can be used. Among them, acetone and isopropyl alcohol are preferred in the case of PVDF polymerization and, in the case of thermoplastic elastomer polymerization, isopentane, diethyl malonate and ethyl acetate are preferred from the viewpoint that the rate of reaction is hardly lowered thereby, and $I(CF_2)_4I$, $I(CF_2)_6I$, $ICH_2I$ and like diiodide compounds are preferred from the viewpoint that the polymer termini can be iodinated and the polymer can be used as a reactive one.

The chain transfer agent is used generally in an amount of $0.5 \times 10^{-3}$ to $5 \times 10^{-3}$ mole percent, preferably $1.0 \times 10^{-3}$ to $3.5 \times 10^{-3}$ mole percent relative to the total feed of the monomers.

In the polymerization of the elastomeric polymer, the polymerization of PVDF can be preferably carried out using a paraffin wax or the like as an emulsion stabilizer, and the polymerization of the thermoplastic elastomer can be preferably carried out using a phosphate salt, sodium hydroxide, potassium hydroxide or the like as a pH adjusting agent.

At the time when the polymerization is complete, the elastomeric polymer obtained by the production method of the invention generally has an average particle diameter of 0.03 to 1 µm, preferably 0.05 to 0.5 µm and a number average molecular weight of 1,000 to 2,000,000; the solid concentration is 10 to 40% by mass.

The elastomeric polymer obtained by the production method of the invention can be converted, according to need, to an aqueous dispersion suited for rubber molding process by adding a dispersion stabilizer such as a hydrocarbon surfactant, and concentrating, for instance. The aqueous dispersion is treated by pH adjustment, coagulation, heating, etc. The respective treatments are carried out in the following manner.

The pH adjustment consists in adjusting the pH to 2 or below by adding a mineral acid such as nitric acid, sulfuric acid, hydrochloric acid or phosphoric acid and/or a carboxylic acid containing not more than 5 carbon atoms and having a pK=4.2 or below, for instance.

The coagulation is carried out by adding an alkaline earth metal salt. As the alkaline earth metal salt, there may be mentioned calcium or magnesium nitrate, chlorate and acetate.

Either of the pH adjustment and the coagulation may be carried out first. Preferably, however, the pH adjustment is carried out first.

After both procedures, the elastomer is washed with an equal volume of water to remove the buffer solution, salt and other impurities occurring in slight amounts within the elastomer, followed by drying. The drying is generally carried out in a drying oven at elevated temperatures of about 70 to 200° C. under circulating hot air.

The fluoropolymer aqueous dispersion according to the invention has fluoropolymer particles having an average primary particle size of 50 to 500 nm dispersed in the aqueous medium in the presence of the above-described compound (a).

The fluoropolymer aqueous dispersion according to the invention preferably has a concentration of fluoropolymer particles of 5 to 70% by mass, and more preferably 30 to 70% by mass.

The aqueous dispersion according to the invention preferably contains the compound of 0.0001 to 2% by mass with respect to the mass of the aqueous medium. A more preferable lower limit of the amount of the compound contained therein is 0.001% by mass and a more preferable upper limit thereof is 0.5% by mass.

The fluoropolymer aqueous dispersion according to the invention may be the dispersion as obtained in the above-described polymerization, or a dispersion solution obtained by concentration or dispersion stabilization treatment of this aqueous dispersion. Further, it may be obtained by dispersing powder of the fluoropolymer obtained by a conventionally known method in the aqueous medium in the presence of the compound (a).

The invention also includes a method of producing the above-mentioned fluoropolymer aqueous dispersion, which includes the step of (I) contacting an aqueous dispersion of a fluoropolymer with an anion exchange resin in the presence of a nonionic surfactant and (II) concentrating the aqueous dispersion obtained in the step (I) so that the aqueous dispersion has a solid content concentration of 30 to 70% by mass with respect to 100% by mass of the aqueous dispersion.

The aqueous dispersion used in the step (I) can be prepared by polymerizing the above-described fluoromonomer, for instance. Contacting with an anion exchange resin can be carried out by a conventionally known method. Further, concentration can be carried out by the above-described method.

The production method according to the invention preferably includes a step of recovering the aqueous dispersion of the fluoropolymer by separating the anion exchange resin after the step (I).

A fine powder of the fluoropolymer of the invention is obtained from the above-mentioned fluoropolymer aqueous dispersion.

The fine powder of the fluoropolymer is obtained by coagulating the fluoropolymer from the above-mentioned fluoropolymer aqueous dispersion and drying, if needed, the obtained fluoropolymer.

The coagulation can be carried out by a conventionally known method. Conditions for the coagulation may be appropriately selected in accordance with the composition and the amount of the fluoropolymer.

Examples of the coagulation method include a method of diluting the fluoropolymer aqueous dispersion with water to a polymer concentration of 10 to 20% by mass, adjusting its pH to neutral or alkaline in some cases, and stirring the dispersion more vigorously compared to the stirring during the reaction in the vessel with a stirrer.

In the coagulation, stirring may be conducted while adding as a coagulant a water-soluble organic compound such as methanol and acetone, an inorganic salt such as potassium nitrate and ammonium carbonate, or an inorganic acid such as hydrochloric acid, sulfuric acid and nitric acid. The coagulation may also be carried out continuously by using an in-line mixer and the like.

Addition of a pigment for coloring or various fillers for improving mechanical characteristics before or during the coagulation can provide a fine powder with a pigment or filler, in which the pigment or filler is uniformly mixed.

The drying is carried out by means of vacuum drying, high-frequency wave, hot blast or the like, in a state where the obtained wet powder does not flow easily, preferably in a state where the obtained wet powder is kept standing.

The drying is carried out at a drying temperature of 10° C. to 250° C., preferably at 100° C. to 200° C.

The friction between powders especially at a high temperature generally has an adverse effect on a fine powder-type PTFE polymer. The reason for this is that the particle comprising PTFE polymers of this type is easily fibrillated by applying even low shear force and loses the original state of a stable particle structure.

The fine powder according to the invention preferably has an average particle size of 300 to 700 μm.

The average particle size is measured in conformity with ASTM D-1457.

The fine powder preferably has an apparent density of 0.35 to 0.65 g/ml.

The apparent density is measured in conformity with JIS K-6891.

The invention also includes a method of recovering the compound (a), which includes the steps of recovering the compound (a) from wastewater and/or gas generated in the step of producing the fine powder, and purifying the recovered compound (a).

The recovering and purifying can be carried out by conventionally known methods.

The uses of the fluoropolymer obtained by the production method of the invention are not particularly restricted but, when it is applied as the aqueous dispersion, the following uses may be mentioned among others: coating of a substrate which comprises applying it to the substrate and drying the coatings, if necessary followed by baking; impregnation process which comprises impregnating a porous support, such as nonwoven fabrics, resin moldings and other porous supports, with the dispersion, followed by drying, if necessary further followed by baking; and cast film formation which comprises applying the dispersion onto a substrate such as a glass, drying the coated substrate and, if necessary after immersion in water, peeling off the coating from the substrate to give a thin film or membrane In these applications, the dispersion is used as an aqueous dispersion type coating composition, an electrode binder, or a water repellent composition for electrodes, for instance.

The fluoropolymer in the form of the aqueous dispersion can be used as an aqueous coating composition after incorporation of one or more known formulating ingredients selected from among pigments, thickening agents, dispersing agents, antifoaming agents, antifreezing agents, film-forming auxiliaries and the like and/or further compounding of another polymeric compound.

The fine powder of the fluoropolymer is preferably used as a molding material. Suitable applications of such a fine powder include hydraulic- or fuel-system tubes in air crafts and vehicles, a flexible hose for chemicals or steam, and wire coating applications.

Effects of the Invention

The compound according to the invention is useful in producing a fluoropolymer.

BEST MODES FOR CARRYING OUT THE INVENTION

The following synthesis examples and working examples will illustrate the invention. These synthesis examples and working examples are, however, by no means limitative of the scope of the invention.

The methods used for the measurements in the respective examples are shown below.

Solid content concentration: Determined based on the weight loss after 1 hour of drying of each aqueous dispersion at 150° C.

Standard specific gravity (SSG): Measured according to ASTM D-1457-69.

Average primary particle size: Determined indirectly from the transmittance, per unit length of the dispersion, of the incident light of 550 nm through the dispersion diluted to a solid content concentration of about 0.02% by mass based on a working curve constructed by plotting such transmittance data against the average particle size data obtained from electron photomicrographs.

SYNTHESIS EXAMPLE 1

A 100-mL three-necked glass flask equipped with a reflux tube and thermometer was charged with 40 g of 15% KOH aqueous solution. Under stirring, 17.6 g of $CF_2$=$CFCF_2COOH$ (disclosed in Japanese Patent Publication S58-52700 (Kokoku)) was added to the solution dropwise to prepare a 37% aqueous solution of $CF_2$=$CFCF_2COOK$.

Subsequently, 15 g of $CF_3CF_2CH_2OH$ was added to the solution dropwise and the inside temperature was maintained at 80° C. Three hours later, the disappearance of a peak of $CF_3CF_2CH_2OH$ was confirmed by using gas chromatography [GC] and reaction was terminated. Further, after cooling the solution to room temperature, pH was adjusted to 1 by using an excess of HCl and the solution was separated to an oil phase and an aqueous phase. Then, the oil phase was recovered and washed with deionized water to obtain 30 g of $CF_3CF_2CH_2OCF_2CFHCF_2COOH$. This was neutralized with ammonia water to obtain $CF_3CF_2CH_2OCF_2CFHCF_2COONH_4$.

SYNTHESIS EXAMPLE 2

A 100-ml PFA-made vessel equipped with a gas inlet pipe was charged with 20 g of the $CF_3CF_2CH_2OCF_2CFHCF_2COOH$ prepared in Synthesis Example 1, and nitrogen was passed through the vessel at a flow rate of 20 ml/minute for 10 minutes to eliminate oxygen and moisture from the system. Fluorine gas diluted to 24% with nitrogen was passed through the vessel warmed on a water bath at 60° C. at a flow rate of 40 ml/minute for 16 hours. After substitution of the vessel inside atmosphere with nitrogen, 19 g of the reaction product was recovered.

This reaction product was rectified at $1.0 \times 10^4$ Pa to give a fraction 1 (boiling point 60° C.) and a fraction 2 (boiling point 78° C.).

NMR analysis clarified that the fraction 1 was $CF_3CF_2CF_2OCF_2CF_2CF_2COOH$ and the fraction 2 was $CF_3CF_2CHFOCF_2CHFCF_2COOH$. These were neutralized with ammonia so that $CF_3CF_2CF_2OCF_2CF_2CF_2COONH_4$ and $CF_3CF_2CHFOCF_2CHFCF_2COONH_4$ were obtained.

EXAMPLE 1

Preparation of PTFE Latex

A 3-L stainless steel autoclave equipped with a stirring blade was charged with 1.5 L of deionized water, 60 g of paraffin wax (melting point 60° C.) and 1.5 g of $CF_3CF_2CF_2OCF_2CF_2CF_2COONH_4$, and the system inside was substituted with TFE. The inside temperature was raised to 70° C., TFE was fed under pressure to an inside pressure of 0.78 MPa, and 3.75 g of a 1% (by mass) aqueous solution of ammonium persulfate [APS] was fed to initiate the reaction. To compensate the pressure reduction in the polymerization system with the progress of the polymerization, TFE was continuously fed to maintain the inside pressure at 0.78 MPa and, in this manner, the reaction was continued. At 7.5 hours after the start of polymerization, TFE was purged away to terminate the polymerization. The solid content concentration of the aqueous dispersion obtained was 30.2% by mass, the standard specific gravity was 2.210, and the average primary particle size of the fluorine-containing polymer was 280 nm.

EXAMPLE 2

Preparation of PTFE Latex

The reaction was carried out in the same manner as in Example 1, except that $CF_3CF_2CF_2OCF_2CF_2CF_2COONH_4$ in Example 1 was changed to $CF_3CF_2CHFOCF_2CHFCF_2COONH_4$ obtained in Synthesis Example 2. At 6.2 hours after the start of polymerization, TFE was purged away to terminate the polymerization. The solid content concentration of the aqueous dispersion obtained was 32.1% by mass, the standard specific gravity was 2.196, and the average primary particle size of the fluorine-containing polymer was 250 nm.

INDUSTRIAL APPLICABILITY

The compound according to the invention is useful as a surfactant or an intermediate to produce a surfactant.

The invention claimed is:

1. A method of producing a fluorine-containing compound comprising the steps of:
    (1) adding, to a compound (a1), a compound (a2) in an aqueous medium under an alkaline condition to obtain a compound (a3),
    the compound (a1) represented by $CF_2$=$CF$—$Rf^2$—$X$, wherein $Rf^2$ represents a fluoroalkylene group containing 1 to 3 carbon atoms, X represents —COOM or —$SO_3M$, and M represents one of H, K, Na, or $NH_4$,
    the compound (a2) represented by $Rf^1$—$CH_2OH$, wherein $Rf^1$ represents a fluoroalkyl group containing 1 to 5 carbon atoms and
    the compound (a3) represented by $Rf^1$—$CH_2$—O—$CF_2$—CHF—$Rf^2$—X, wherein $Rf^1$, $Rf^2$, and X are as defined above; and
    (2) fluorinating the compound (a3) to obtain the fluorine-containing compound,
    the fluorine-containing compound represented by $Rf^3$—O—$CF_2$—$Rf^4$—X, wherein $Rf^3$ represents a fluoroalkyl group containing 1 to 6 carbon atoms, $Rf^4$ represents a fluoroalkylene group containing 1 to 4 carbon atoms, and X is as defined above.

2. The method of producing a fluorine-containing compound according to claim 1,
    wherein $Rf^1$ in the compound (a2) is a fluoroalkyl group containing 1 to 3 carbon atoms.

* * * * *